United States Patent [19]

El-Nokaly et al.

[11] Patent Number: 6,013,269

[45] Date of Patent: *Jan. 11, 2000

[54] COSMETIC MAKE-UP COMPOSITIONS

[75] Inventors: Magda El-Nokaly, Cincinnati, Ohio; Kataline Igo-Kemenes, Thorpe Green; David Andrew Jakubovic, Staines, both of United Kingdom; Michael Lee Vatter, Okeana, Ohio

[73] Assignee: The Procter & Gamble Company, Cincinnati, Ohio

[ * ] Notice: This patent is subject to a terminal disclaimer.

[21] Appl. No.: 08/817,155

[22] PCT Filed: Sep. 18, 1995

[86] PCT No.: PCT/US95/11830

§ 371 Date: Feb. 5, 1998

§ 102(e) Date: Feb. 5, 1998

[87] PCT Pub. No.: WO96/11665

PCT Pub. Date: Apr. 25, 1996

[30] Foreign Application Priority Data

Oct. 12, 1994 [GB] United Kingdom .................... 9420535

[51] Int. Cl.[7] ................................ A61K 6/00; A61K 7/00; A61K 31/74
[52] U.S. Cl. .......................................... 424/401; 424/78.03
[58] Field of Search ................................. 424/78.03, 401; 514/937

[56] References Cited

U.S. PATENT DOCUMENTS

| 3,444,291 | 5/1969 | Bivins | 424/63 |
| 3,978,207 | 8/1976 | Fotiu et al. | 424/63 |
| 4,486,405 | 12/1984 | Klein | 424/59 |
| 4,659,562 | 4/1987 | Arraudeau et al. | 424/63 |
| 4,767,625 | 8/1988 | Mitsuno et al. | 424/95 |
| 4,804,532 | 2/1989 | Busch, Jr. | 424/69 |
| 4,999,348 | 3/1991 | Cioca et al. | 514/171 |
| 5,085,856 | 2/1992 | Dunphy et al. | 424/64 |
| 5,143,722 | 9/1992 | Hollenberg et al. | 424/63 |
| 5,688,831 | 11/1997 | El-Nokaly et al. | 514/938 |

OTHER PUBLICATIONS

Nakamura et al., "Blurring of Wrinkles Through Control of Optical Properties", Preprints of the XIVth I.F.S.C.C. Congress, Barcelona, vol. 1, pp. 51–63 (1986).

Primary Examiner—Thurman K. Page
Assistant Examiner—Sharon Howard
Attorney, Agent, or Firm—Loretta J. Henderson; T. David Reed; Michael E. Hilton

[57] ABSTRACT

A make-up comosition in the form of an oil-in-water emulsion comprising volatile silicone or hydrocarbon oil, pigment, organic amphiphilic material capable of forming smectic lyotropic liquid crystals in product or on the skin, and optionally, non-volatile oil. The make-up composition exhibits improved moisturisation and product stability together with reduced shine.

34 Claims, No Drawings

# COSMETIC MAKE-UP COMPOSITIONS

This application is a 371 of PCT/US95/11830 Sep. 18, 1995.

FIELD OF THE INVENTION

The present invention relates to cosmetic make-up compositions and more particularly, to pigmented foundation make-up compositions and blushers having improved product stability, oil/shine control and moisturisation effectiveness. The compositions incorporate an amphiphilic material which is capable of forming liquid crystals.

BACKGROUND OF THE INVENTION

A foundation composition can be applied to the face and other parts of the body to even skin tone and texture and to hide pores, imperfections, fine lines and the like. A foundation composition is also applied to moisturize the skin, to balance the oil level of the skin and to provide protection against the adverse effects of sunlight, wind and the harsh environment.

Make-up compositions are generally available in the form of liquid or cream suspensions, emulsions, gels, pressed powders or anhydrous oil and wax compositions.

U.S. Pat. No. 3,444,291 discloses a method of filling and camouflaging skin cavities by applying a composition which includes 65 to 75 parts by weight of a microcrystalline wax and about 25 to 35 parts of a mineral oil. The composition includes a colourant, preferably a coal tar dye, for example, D &C Red No. 17, which matches the colour of the user's skin.

A spreadable, flowable and greaseless cosmetic cover-up composition is taught in U.S. Pat. No 4,486,405. That composition is characterized by the presence of a first and a second alkoxylated surfactant present in substantially the same concentration.

U.S. Pat. No. 4,804,532 recites a facial cosmetic powder which utilizes crystalline silica in much lower concentration than that employed in the then prior art compositions. This powder, used as a blush or a facial coating, is said to be effective in hiding skin wrinkles, lines and pores. The composition is a mixture of a colour phase and a diluent phase. The colour phase is formed by blending crystalline silica with colourants. The resultant colour phase is mixed with the diluent phase, essentially formed from nacreous materials such as talc and mica, to form the composition.

The use of a foundation composition which has a significantly high concentration of nacreous material is taught in U.S. Pat. No. 3,978,207. This foundation, a pressed powder composition, is characterized by the presence of a nacreous material such as mica and a binder oil which provides a frosted pearl effect, that is, a lustrous look. The colour of this foundation is provided by the nacreous material.

U.S. Pat. No. 4,659,562 discloses a cosmetic make-up composition which includes, as a binding agent therefore, an intimate mixture of from 5 to 95 weight percent of a mixture of finely divided silica and about 5 to 95 weight percent of finely divided polyethylene fibres. The composition is recited to maintain its uniformity over the areas of the skin to which it is applied. That is, it is said to be "creaseproof". The composition of the '562 patent includes colourant in admixture with nacreous agents.

Nakamura et al., Preprints of the XIVth I.F.S.C.C. Congress, Barcelona, 1986, Vol. I, 51–63 (1986) describes a novel make-up composition utilizing spherical silica and polydimethyl siloxane. This combination is recited to provide a foundation which reduces wrinkle visibility to a greater extent than make-up foundations with which it was compared. This reduction in wrinkle visibility is caused by optical blurring enhanced by the novel use of spherical silica and polydimethyl siloxane.

U.S. Pat. No. 5,143,722 discloses a cosmetic make-up composition comprising water-in-oil emulsions comprising pigment coated with polysiloxane, a silicone phase, a water phase and a polydiorganosiloxane-polyoxyalkylene copolymeric surfactant.

Foundations in the form of oil-in-water emulsions are well known in the art. These have, however, not been successful from the viewpoint of moisturisation and shine/oil control.

In the past, humectants such as water-soluble polyglycerylmethacrylate lubricants and glycerine have been incorporated into skin and hair gel compositions for use as moisturisation agents. These compositions have provided improvements in moisturisation, absorption, skin feel, residue and skin care characteristics compared with conventional cosmetic cream and lotion compositions. There is still a need, however, for enhanced moisturisation both in the short and longer term and also increased emulsion stability and oil/shine control.

Liquid crystals are a special phase of matter. The liquid crystal phase exists between the boundaries of the solid phase and the isotropic liquid phase (i.e. an intermediate between the three dimensionally ordered crystalline state and the disordered dissolved state). In the liquid crystal state, some of the molecular order characteristics of the solid phase are retained in the liquid state because of molecular association structure and long range intermolecular order. The ability of some compounds to form a liquid crystalline mesophase had been observed nearly a century ago. Since that time many compounds exhibiting liquid crystalline properties have been synthesized and have been used to encapsulate and act as a delivery vehicle for drugs, flavours, nutrients and other compounds.

It is accordingly a primary object of this invention to provide a make-up composition in the form of an oil-in-water emulsion comprising an amphiphilic material capable of forming liquid crystals.

It is also an object of the invention to provide a pigmented make-up composition in the form of an oil-in-water emulsion which exhibits improved moisturisation together with good product stability and reduced shine.

SUMMARY OF THE INVENTION

According to the present invention there is provided a make-up composition in the form of an oil-in-water emulsion comprising:
  (a) from about 1% to about 30% by weight of volatile silicone oil and/or volatile hydrocarbon oil;
  (b) from about 0% to about 20% by weight of non-volatile oil;
  (c) from about 5% to about 25% by weight of pigment; and
  (d) from about 0.1% to about 20% by weight of organic amphiphilic material which is capable of forming smectic lyotropic liquid crystals in product or on the skin;
wherein the ratio of (a) to (d) is at least about 1.5:1.

The oil-in-water emulsions of the present invention provide improved moisturisation together with excellent product stability and reduced shine.

All levels and ratios are by weight of total composition, unless otherwise indicated. Chain length and degrees of alkoxylation are also specified on a weight average basis.

DETAILED DESCRIPTION OF THE INVENTION

The make-up composition according to the present invention comprises volatile silicone oil and/or hydrocarbon oil, pigment, organic amphiphilic material capable of forming lyotropic liquid crystals in product or on the skin and optionally, non-volatile oil. The composition is in the form of an oil-in-water emulsion.

A first essential component of the oil-in-water emulsion is a volatile silicone oil or hydrocarbon oil. The silicone oil or hydrocarbon oil is present in an amount of from about 0.1% to about 30%, preferably at least about 20%, especially at least about 25% by weight. Suitable volatile silicone oils include cyclic and linear volatile polyorganosiloxanes. As used herein, "volatile" refers to those materials which have a vapour pressure greater than that of cetyl alcohol at 25° C., and preferably have a vapour pressure of at least 1 mmHg at 100° C. or less, preferably at 60° C. or less. "Non-volatile" refers to those materials which have a vapour pressure at least equal to cetyl alcohol at 25° C. (see the description of various volatile silicones in Todd, et al.. "Volatile Silicone Fluids for Cosmetics", 91 Cosmetics and Toiletries 27–32 (1976)).

Preferred cyclic silicones include polydimethylsiloxanes containing from about 3 to about 9 silicon atoms, preferably containing from about 4 to about 5 silicon atoms. Preferred linear silicone oils include the polydimethylsiloxanes containing from about 3 to about 9 silicon atoms. The linear volatile silicones generally have viscosities of less than about 5 centistokes at 25° C., while the cyclic materials have viscosities of less than about 10 centistokes. Examples of silicone oils useful in the present invention include: Dow Corning 344, Dow Corning 21330, Dow Corning 345, and Dow Corning 200 (manufactured by the Dow Corning Corporation): Silicone 7207 and Silicone 7158 (manufactured by the Union Carbide Corporation). SF:202 (manufactured by General Electric) and SWS-03314 (manufactured by Stauffer Chemical), preferably Dow Corning 21330 (CTFA designation: cyclomethicone).

Suitable volatile hydrocarbon oils for use herein include isododecane, isohexadecane, isoeicosane, isodecane, decane, hexadecane, dodecane, tetradecane and octadecane. Particularly suitable for use herein are branched chain aliphatic hydrocarbons sold under the trade name Permethyl (RTM) and commercially available from Presperse Inc., P.O. Box 735, South Plainfield, N.J. 07080, U.S.A.

A second component which is preferably incorporated in the compositions of the invention is a non-volatile oil. Suitable non-volatile oils can be selected from hydrocarbon waxes and oils, microcrystalline waxes, silicone waxes, esters of fatty acids with fatty alcohols and polyalkylene glycol ethers of fatty alcohols, and mixtures thereof. Suitable hydrocarbons for use herein include paraffin oil, soft paraffin wax and petrolatum. Preferred non-volatile oils for use herein are esters of fatty acids with fatty alcohols and polyalkylene glycol ethers of fatty alcohols. The alcohol portion of the esters suitable for use herein include methanol, isobutanol, 2-ethylhexanol, isopropanol, ethylene glycol, polyethylene glycol, glycerol, diglycerol, xylitol, erythritol, pentaerythritol, sucrose, sorbitol or sorbitan. The fatty acid portion of the esters suitable for use herein include lauric acid, myristic acid, palmitic acid stearic acid, oleic acid and behenic acid. Especially preferred from the viewpoint of moisturisation are optionally hydroxy substituted $C_8$–$C_{50}$ unsaturated fatty acids or esters thereof, e.g. cetyl ricinoleate, and PPG-2 myristyl ether propionate, and mixtures thereof. The non-volatile oil is present in the compositions at a level of from about 0% to about 20%, preferably from about 0.1% to about 10%, more preferably from about 2% to about 6%, by weight.

In preferred embodiments the non-volatile oil comprises a wax or mixture of waxes and liquid oils having a melting completion temperature of at least about 30° C.

A further essential component of the compositions herein is an organic amphiphilic material which is capable of forming smectic lyotropic crystals in product or when the product is applied on the skin at ambient or elevated temperatures. Preferably the amphiphilic material is capable of forming smectic lyotropic liquid crystals at a temperature in the range from about 20° C. to about 40° C. The amphiphilic material is present at a level of from about 0.1% to about 20%, preferably from about 0.1% to about 15%, by weight.

The liquid-crystal forming amphiphilic materials suitable for use herein contain both hydrophilic and lipophilic groupings and exhibit a marked tendency to adsorb at a surface or interface, i.e. they are surface-active. Surface-active materials are divided into nonionic (no charge), anionic (negative charge), cationic (positive charge) and amphoteric (both charges) based on whether or not they ionize in aqueous media.

In the literature, liquid crystals are also referred to as anisotropic fluids, a fourth state of matter, surfactant association structure or mesophases. Those terms are often used interchangeably. The term "liquid crystals" as used herein means "smectic lyotropic liquid crystals" unless otherwise specified. The term "lyotropic" herein means a liquid crystalline system containing a solvent. In preferred embodiments herein the polar solvent is water or a solution of humectant in water. Smectic lyotropic liquid crystals are to be distinguished from thermotropic, heat, magnetically induced or cholesteric liquid crystals. The liquid crystals used herein are preferably lamellar, hexagonal, rod or vesicle structures or mixtures thereof The liquid crystalline phase utilized in the compositions of the invention can be identified in various ways. A liquid crystal phase flows under shear and is characterised by a viscosity that is significantly different from the viscosity of its isotropic solution phase. Rigid gels do not flow under shear like liquid crystals. Also, when viewed with a polarized light microscope, liquid crystals show identifiable birefringence, as, for example, planar lamellar birefringence, whereas when isotropic solutions and rigid gels are viewed under polarized light, both show dark fields.

Other suitable means for identifying liquid crystals include X-ray diffraction, NMR spectroscopy and transmission electron microscopy.

In general terms, the organic amphiphilic material preferred for use herein can be described as a liquid, semi-solid or waxy water-dispersible material having the formula X-Y where X represents a hydrophilic, especially nonionic moiety and Y represents a lipophilic moiety.

Organic amphiphilic materials suitable for use herein include those having a weight average HLB (Hydrophilic Lipophilic Balance) in the range from about 2 to about 15, preferably from about 8 to about 15.

Preferred organic amphiphilic materials employed herein have a long saturated or unsaturated branched or linear lipophilic chain having from about 12 to about 30 carbon atoms such as oleic, lanolic, tetradecylic, hexadecylic, isostearylic, lauric or alkyl phenyl chains. When the hydrophilic group of the amphiphilic material forming the liquid crystal phase is a nonionic group, a polyoxyethylene, a polyglycerol, a polyol ester, oxyalkylated or not, and, for example, a polyoxyalkylated sorbitol or sugar ester, can be employed. When the hydrophilic group of the amphiphilic material forming the liquid crystal phase is an ionic group, advantageously there can be used, as the hydrophilic group, a phosphatidylcholine residue as found in lecithin.

Nonionic amphiphilic components preferred for use herein are selected from:

(1) ethers of linear, or branched, polyglycerol having the following formula:

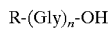

wherein n is a whole number between 1 and 6, R is selected from aliphatic, linear or branched, saturated or unsaturated chains of 12 to 30 carbon atoms, the hydrocarbon radicals of lanolin alcohols and the 2-hydroxy alkyl residue of long chain, alpha-diols, and Gly represents a glycerol residue;

(2) polyethoxylated fatty alcohols, for example those of the formula $R^1$ $(C_2R_4O)_xOH$ wherein $R^1$ is $C_{12}$–$C_{30}$ linear or branched alkyl or alkenyl and x averages from about 0 to about 20, preferably from about 0.1 to about 6, more preferably from about 1 to about 4;

(3) polyol esters and polyalkoxylated polyol esters, and mixtures thereof, the polyols preferably being selected from sugars, $C_2$–$C_6$ alkylene glycols, glycerol, polyglycerols, sorbitol, sorbitan, polyethylene glycols and polypropylene glycols and wherein the polyalkoxylated polyol esters contain from about 2 to about 20 preferably from about 2 to about 4 moles of alkylene oxide (especially ethylene oxide) per mole of polyol ester;

(4) natural and synthetic phosphoglycerides, glycolipids and sphingolipids, for example cerebrosides, ceramides and lecithin.

Examples of other organic amphiphilic materials suitable for use herein include $C_8$–$C_{30}$ alkyl and acyl-containing amphoteric, anionic, cationic and nonionic surfactants as set out below.

Amphoteric
N-alkyl amino acids (e.g., sodium N-alkylaminoacetate);
N-lauroylglutamic acid cholesterol ester (e.g., Eldew CL-301 Ajinomoto)
Anionic
Acylglutamates (e.g., disodium N-lauroylglutamate);
Sarcosinates (e.g., sodium lauryl sarcosinate. Grace, Seppic);
Taurates (e.g., sodium lauryl taurate. sodium methyl cocoyl taurate);
Carboxylic acids and salts (e.g., potassium oleate; potassium laurate;
potassium-10-undecenoate; potassium 11-(p-styryl) -undecanoate);
Ethoxylated carboxylic salts (e.g., sodium carboxy methyl alkyl ethoxylate);
Ether carboxylic acids;
Phosphoric acid esters and salts (e.g., lecithin; DEA-oleth-10 phosphate);
Acyl isethionates (e.g., sodium 2-lauroyloxyethane sulfonate);
Alkane sulfonates (e.g., branched sodium x-alkane sulfonate (x/1);

Sulfosuccinates e.g.,
    Sodium dibutyl sulfosuccinate,
    Sodium di-2-pentyl sulfosuccinate,
    Sodium di-2-ethylbutyl sulfosuccinate,
    Sodium di-hexyl-sulfosuccinate,
    Sodium di-2 ethylhexyl sulfosuccinate (AOT),
    Sodium di-2-ethyldodecyl sulfosuccinate,
    Sodium di-2-ethyloctadecyl sulfosuccinate,
    Dioctyl sodium sulfosuccinate,
    Disodium laureth sulfosuccinate (MacKanate E1, McIntyre Group Ltd.)
Sulfric acid esters (e.g., sodium 2-ethylhept-6-enyl sulfate; sodium 11-heneicosyl sulfate; sodium 9-heptadecyl sulfate).
Alkyl sulfates (e.g., MEA alkyl sulfate such as MEA-lauryl sulfate)
Cationic
Alkyl Imidazolines (e.g., alkyl hydroxyethyl imidazoline, stearyl hydroxyethyl imidazoline (supplier Akzo, Finetex and Hoechst));
Ethoxylated Amines (e.g., PEG-n alkylamine, PEG-n alkylamino propylamine, Poloxamine, PEG-cocopolyamine, PEG-15 tallow amine);
Alkylamines (e.g., dimethyl alkylamine; dihydroxyethyl alkylamine dioleate)
Quaternaries
Alkylbenzyl dimethylammonium salts (e.g., stearalkonium chloride);
Alkyl betaines (e.g., dodecyl dimethyl ammonio acetate, oleyl betaine);
Heterocylic ammonium salts (e.g., alkylethyl morpholinium ethosulfate);
Tetraalkylammonium salts (e.g., dimethyl distearyl quaternary ammonium chloride (Witco));
Bis-isosteardmidopropyl hydroxypropyl diammonium chloride (Schercoquat 21AP from Scher Chemicals);
1.8-Bis (decyldimethylammnonio)-3,6 dioxaoctane ditosylate
Nonionic Surfactants
Ethoxylated glycerides;
Monoglycerides (e.g., monoolein; monolinolein; monolaurin; 1-dodecanoyl-glycerol monolaurin; 1,13-docosenoyl-glycerol monoerucin diglyceride fatty acid (e.g., diglycerol monoisostearate Cosmol 41, fractionated. Nisshin Oil Mills Ltd.);
Polyglyceryl esters (e.g., triglycerol monooleate (Grindsted TS-T122), diglycerol monooleate (Grindsted TST-T101);
Polyhydric alcohol esters and ethers (e.g., sucrose monooleate (Ryoto, Mitsubishi-Kasei Food Corporation), cetostearyl glucoside (Montanol, Seppic), βoctyl glucofuranoside esters, alkyl glucoside such $C_{10}$–$C_{16}$ (Henkel));
Diesters of phosphoric acid (e.g., sodium dioleyl phosphate);
Alkylamido propyl betaine (e.g., cocoamido propyl betaine);
Amide: (e.g., N-(dodecanoylaminoethyl)-2-pyrrolidone);
Amide oxide: e.g., 1,1 Dihydroperfluorooctyldimethylamine oxide,
    Dodecyldimethylamine oxide,
    2-Hydroxydodecyldimethylamine oxide,
    2-Hydroxydodecyl-bis (2-hydroxyethyl) amine oxide,
    2-Hydroxy-4-oxahexadecyldimethylamine oxide,
Ethoxylated amides (e.g., PEG-n acylamide);
Ammonio phosphates (e.g., didecanoyl lecithin);
Amine (e.g., octylamine);

Ammonio amides e.g.,
  N-trimethylammoniodecanamidate,
  N-trimethylammoniododecanamidate,
Ammonio carboxylates e.g.,
  dodecyldimethylannmonioacetate,
  6-didodecylmethylammoniohexanoate,
Phosphonic and phosphoric esters and amides e.g.,
  methyl-N-methyl-dodecylphosphonamidate,
  dimethyl dodecylphosphonate,
  dodecyl methyl methylphosphonate,
  N,N-dimethyl dodecylphosphonic diamide
Ethoxylated alcohols
Polyoxyethylene ($C_8$) e.g.,
  pentaoxyethylene glycol p-n-octylphenyl ether
  hexaoxyethylene glycol p-n-octylphenyl ether
  nonaoxyethylene glycol p-n-octylphenyl ether
Polyoxyethylene ($C_{10}$) e.g.,
  pentaoxyethylene glycol p-n-decylphenyl ether,
  decyl glyceryl ether, 4-oxatetradecan-1,2-diol,
  nonaoxyethylene glycol p-n-decylphenyl ether
Polyoxyethylene ($C_{11}$) e.g.,
  Tetraoxyethylene glycol undecyl ether
Polyoxyethylene ($C_{12}$) e.g.,
  3,6,9,13-tetraoxapentacosan 1,11-diol,
  3,6,10-trioradocosan-1,8-diol,
  3,6,9,12,16-pentaoxaoctacosan 1,14-diol,
  3,6,9,12,15-pentaoxanonacosan-1,17-diol,
  3,7-dioxanonadecan-1,5-diol,
  3,6,12,15,19-hexaoxahentriacontan-1,16-diol,
  pentaoxyethylene glycol dodecyl ether,
  pentaoxyethylene glycol p-n-dodecylphenyl ether,
Polyoxyethylene($C_{14}$) e.g.,
  3,6,9,12,16-pentaoxaoctacosan-1,14-diol,
  3,6,9,12,15,19-heraoxatriacontan-1,17-diol,
Sulfone diimines e.g.,
  decyl methyl sulfone diimine
Sulfoxides e.g.,
  3-decyloxy-2-hydroxypropyl methyl sulfoxide
  4-decyloxy-3-hydroxybutyl methyl sulfoxide
Sulfoximines e.g.,
  N-methyl dodecyl methyl sulfoximine Highly preferred organic amphiphilic materials for use herein are selected from sugar esters and polyalkoxylated sugar esters and phophatides such as lecithin.

The sugar esters for use in this invention can be classified as hydrocarbyl and alkyl polyoxyalkylene esters of cyclic polyhydroxy saccharides wherein one or more of the hydroxyl groups on the saccharide moiety is substituted with an acyl or polyoxyalkylene group. Hydrocarbyl sugar esters can be prepared in well-known fashion by heating an acid or acid halide with sugar, i.e., by a simple esterification reaction.

The sugars employed in the preparation of the sugar esters include monosaccharides, di-saccharides and oligo-saccharides well known in the art, for example, the dextrorotatory and levorotatory forms of glucose, fructose, mannose, galactose, arabinose and xylose. Typical di-saccharides include maltose, cellibiose, lactose, and trehalose. Typical tri-saccharides include raffinose and gentianose. The monosaccharides are preferred for use herein, especially sucrose.

Sucrose can be esterified at one or more of its eight hydroxyl groups to provide the sucrose esters useful herein. When sucrose is combined with an esterification agent in a 1:1 mole ratio, sucrose monoesters are formed; when the ratio of esterification agent to sucrose is 2:1, or greater, the di-, tri-, etc., esters are formed, up to a maximum of the octa-ester.

Preferred sugar esters herein are those prepared by the esterification of sugars at a mole ratio of esterification agent:sugar of 1:1 and 3:1 i.e., the mono-acyl and di- or tri-acyl sugar esters. Especially preferred are the mono-, di- and tri-acyl sugar esters and mixtures thereof wherein the acyl substituents contain from about 8 to about 20 carbon atoms and 0,1 or 2 unsaturated moieties. Of the mono-acyl and di-acyl sugar esters, the respective esters of di-saccharide sugars, especially sucrose, wherein the acyl groups contain from about 8 to about 20 carbon atoms are especially preferred. Preferred sugar esters herein are sucrose monooctanoate, sucrose monodecanoate, sucrose monolaurate, sucrose monomyristate, sucrose monopalmitate, sucrose monostearate, sucrose monooleate, sucrose monolinoleate, sucrose dioleate, sucrose dipalmitate, sucrose distearate, sucrose dilaurate and sucrose dilinoleate, and mixtures thereof. Sucrose oleates, laurates and palmitates have been found to be particularly efficacious in the compositions herein, especially sucrose monooleate and sucrose dilaurate. In mixtures of mono-acyl with di-, tri- and higher acyl sugar esters, the mono- and di-acyl esters preferably comprise at least about 40%, more preferably from about 50% to about 95% by weight of the total sugar ester mixture.

Other sugar esters suitable for use in the compositions of this invention are the alkyl polyoxyalkylene sugar esters wherein one hydroxyl group is substituted with a $C_8$–$C_{18}$ alkyl group and wherein one or more of the hydroxyl groups on the sugar molecule are replaced by an ester or ether substituent containing the moiety $[(CH_2)_x—O]_y$ wherein x is an integer from 2 to about 4, preferably 2, and wherein y is an integer from about 1 to about 50, preferably 8 to 30 polyoxyalkylene substituents. Especially preferred herein are sugar esters wherein the polyoxyalkylene substituent is a polyoxyethylene substituent containing from about 8 to about 30 polyoxyethylene groups. Such materials wherein sorbitan is the sugar moiety are commercially available under the tradename "Tweens". Such mixed esters can be prepared by first acylating a sugar at a 1:1 mole ratio with a hydrocarbyl acid halide followed by reaction with the corresponding polyoxyalkylene acid halide or alkylene oxide to provide the desired material. The simple polyoxyalkylene ester of di-saccharides, especially sucrose, wherein the polyoxyalkylene groups contain up to about 20 alkylene oxide moieties are another useful class of sugar esters herein. A preferred sugar ester of this class is sorbitol trioleate ethoxylated with 20 moles of ethylene oxide. Mixtures of sugar esters with other polyol esters, eg. glycerol esters, are also suitable for use herein, for example, Palm Oil Sucroglyceride (Rhone-Poulenc).

As used herein, the term "lecithin" refers to a material which is a phosphatide. Naturally occurring or synthetic phosphatides can be used. Phosphatidylcholine or lecithin is a glycerine esterified with a choline ester of phosphoric acid and two fatty acids, usually a long chain saturated or unsaturated fatty acid having 16–20 carbons and up to 4 double bonds. Other phosphatides capable of forming lamellar or hexagonal liquid crystals can be used in place of the lecithin or in combination with it. These phosphatides are glycerol esters with two fatty acids as in the lecithin, but the choline is replaced by ethanolamine (a cephalin), or serine (aminopropanoic acid; phosphatidyl serine) or an inositol (phosphatidyl inositol). While the invention herein is exemplified with lecithin, it is understood that these other phosphatides can be used herein.

A variety of lecithins can be used. American Lecithin Company supplies a Nattermann Phospholipid, Phospholipan 80 and Phosal 75. Other lecithins which can be used alone or in combination with these are: Actifla Series, Centrocap series, Central Ca, Centrol series, Centrolene, Centrolex, Centromix, Centrophase and Centrolplhil Series from Central Soya; Alcolec and Alcolec 439-C from American Lecithin; Canaspersa from Canada Packers, Lexin K and Natipide from American Lecithin; and L-Clearate, Clearate LV and Clearate WD from the W.A. Cleary Co. Lecithins are supplied dissolved in ethanol, fatty acids, triglycerides and other solvents. They are usually mixtures of lecithins and range from 15% to 50% of the solution as supplied.

Both natural and synthetic lecithins can be used. Natural lecithins are derived from oilseeds such as sunflower seeds, soybeans, safflower seeds and cottonseed. The lecithins are separated from the oil during the refining process.

The organic amphiphilic compound has been found to be especially valuable herein for providing shine/oil control of oil-in-water make-up compositions. While not being limited by theory, it is the ability of the liquid crystals in the compositions to bind sebum from the skin which helps to provide improved shine control.

In the compositions herein the ratio of volatile silicone oil to organic amphiphilic material is at least about 1.5:1.

Another essential component herein is a pigment. Suitable pigments for use herein can be inorganic and/or organic. Also included within the term pigment are materials having a low colour or lustre such as matte finishing agents, and also light scattering agents. Examples of suitable pigments are iron oxides, acylglutamate iron oxides, ultramarine blue, D&C dyes, carmine, and mixtures thereof Depending upon the type of make-up composition, whether foundation or blusher, a mixture of pigments will normally be used.

The foundation composition can also include at least one matte finishing agent. The function of the matte finishing agent is to hide skin defects and reduce shine. Such cosmetically acceptable inorganic agents, i.e., those included in the CTFA Cosmetic Ingredient Dictionary, Third Ed., as silica, hydrated silica, silicone-treated silica beads, mica, talc, polyethylene, titanium dioxide, bentonite, hectorite, kaolin, chalk, diatomaceous earth, attapulgite and the like may be utilized. Of particular usefulness as a matte finishing agent is low lustre pigment such as titanated mica (mica coated with titanium dioxide) coated with barium sulfate. Of the inorganic components useful as a matte finishing agent low lustre pigment, talc, polyethylene, hydrated silica, kaolin, titanium dioxide and mixtures thereof are particularly preferred. Materials suitable for use herein as light-scattering agents can be generally described as spherical shaped inorganic materials having a particle size of up to about 100 microns, preferably from about 5 to about 50 microns, for example spherical silica particles.

The total concentration of the pigment may be from about 5 to about 25% by weight and is preferably from about 5 to about 20% by weight of the total composition, the exact concentration being dependent to some extent upon the specific mixture of pigments selected for use in a foundation make-up or blusher to achieve the desired shades. The preferred compositions contain from about 2% to about 20% by weight of titanium dioxide and most preferably from about 5% to about 10% by weight of titanium dioxide.

Suitable pigments for use herein are treated pigments. The pigments can be treated with compounds such as amino acids, silicones, lecithin and ester oils.

Preferred pigments for use herein are water-dispersible pigments such as those sold under the tradename Softex.

A preferred component of the compositions herein is a humectant. The humectant herein is present in an amount of from about 0.1% to about 20% preferably from about 1% to about 5% by weight of composition. Suitable humectants are selected from glycerine and polyglycerylmethacrylate lubricant having a viscosity at 25° C. of 300,000 to 1,100,000 cps; a specific gravity at 25° C. of 1 to 1.2 g/ml, a pH of 5.0 to 5.5; a bound water content of 33 to 58%; and, a free water content from 5 to 20%.

In preferred embodiments, the humectant is incorporated at least partly into the oil phase of the oil-in-water emulsion so as to form a multiphase humectant-in-oil-in-water dispersion. The oil phase preferably comprises from about 0.1% to about 10%, more preferably from about 0.1% to about 3% by weight of humectant on a composition basis. Suitably, the humectant is introduced into the oil phase in the form of a mixture with or incorporated within a particulate lipophilic or hydrophobic carrier material. Humectant can also be introduced via the liquid crystal internal solvent phase.

Polyglycerylmethacrylate lubricants having the desired properties are marketed by Guardian Chemical Corporation under the trademark "Lubrajel". The "Lubrajels" identified as "Lubrajel DV", "Lubrajel MS", and "Lubrajel CG" are preferred in the present invention. The gelling agents sold under these trademarks contain about 1% propylene glycol.

Other suitable humectants include sorbitol, panthenols, propylene glycol, butylene glycol, hexylene glycol, hyaluronic acid, alkoxylated glucose derivatives, such as Glucam (RTM) E-20, hexanetriol, and glucose ethers, and mixtures thereof. Urea is also suitably added as a humectant in the internal aqueous phase.

The panthenol moisturiser can be selected from D-panthenol ([R]-2,4-dihydroxy-N-[3-hydroxypropyl)]-3,3-dimethelbutamide), DL-panthenol, calcium pantothenate, royal jelly, panthetine, pantotheine, panthenyl ethyl ether, pangamic acid, pyridoxin, pantoyl lactose and Vitamin B complex.

The preferred humectant herein is glycerine. Chemically, glycerine is 1,2,3-propanetriol and is a product of commerce.

The balance of the composition of the present invention is water. The composition preferably comprises from about 10% to about 60%, preferably from about 20% to about 50% by weight of water.

In the compositions of the invention the ratio of organic amphiphilic material to water is preferably in the range from about 2:1 to about 1:6, more preferably from about 1:1 to about 1:5. In preferred embodiments of the invention the ratio of organic amphiphilic material to total oil is in the range from about 5:1 to about 1:5, preferably from about 1:1 to about 1:4.

The make-up compositions of the present invention can also comprise a particulate cross-linked hydrophobic acrylate or methacrylate copolymer. This copolymer is particularly valuable for reducing shine and controlling oil while helping to provide effective moisturization benefits. The cross-linked hydrophobic polymer is preferably in the form of a copolymer lattice with at least one active ingredient dispersed uniformly throughout and entrapped within the copolymer lattice. Alternatively, the hydrophobic polymer can take the form of a porous particle having a surface area ($N_2$-BET) in the range from about 50 to 500, preferably 100 to 3000 $m^2/g$ and having the active ingredient absorbed therein.

The cross-linked hydrophobic polymer when used herein is in an amount of from about 0.1% to about 10% by weight and is preferably incorporated in the internal silicone-containing oil phase. The active ingredient can be one or more or a mixture of skin compatible oils, ski compatible humectants, emollients, moisturizing agents and sunscreens. The polymer material is in the form of a powder, the powder being a combined system of particles. The system of powder particles forms a lattice which includes unit particles of less than about one micron in average diameter, agglomerates of fused unit particles of sized in the range of about 20 to 100 microns in average diameter and aggregates of clusters of fused agglomerates of sizes in the range of about 200 to 1,200 microns in average diameter.

The powder material of the present invention which can be employed as the carrier for the active ingredient can be broadly described as a cross-linked "post absorbed" hydrophobic polymer lattice. The powder preferably has entrapped and dispersed therein, an active which may be in the form of a solid, liquid or gas. The lattice is in particulate form and constitutes free flowing discrete solid particles when loaded with the active material. The lattice may contain a predetermined quantity of the active material. The polymer has the structural formula:

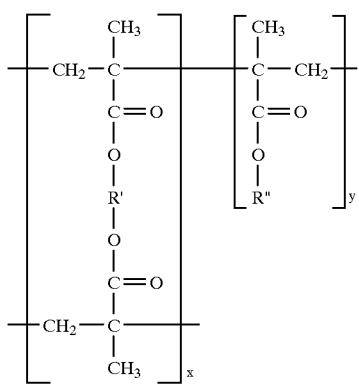

where the ratio of x to y is 80:20, R' is —$CH_2CH_2$— and R" is —$(CH_2)_{11}CH_3$.

The hydrophobic polymer is a highly crosslinked polymer, more particularly a highly cross-linked polymethacrylate copolymer. The material is manufactured by the Dow Corning Corporation, Midland. Mich., USA, and sold under the trademark POLYTRAP (RTM). It is an ultralight free-flowing white powder and the particles are capable of absorbing high levels of lipophilic liquids and some hydrophilic liquids while at the same time maintaining a free-flowing powder character. The powder structure consists of a lattice of unit particles less than one micron that are fused into agglomerates of 20 to 100 microns and the agglomerates are loosely clustered into macro-particles or aggregates of about 200 to about 1200 micron size. The polymer powder is capable of containing as much as four times its weight of fluids, emulsions, dispersions or melted solids.

Adsorption of actives onto the polymer powder can be accomplished using a stainless steel mixing bowl and a spoon, wherein the active is added to the powder and the spoon is used to gently fold the active into the polymer powder. Low viscosity fluids may be adsorbed by addition of the fluids to a sealable vessel containing the polymer and then tumbling the materials until a consistency is achieved. More elaborate blending equipment such as ribbon or twin cone blenders can also be employed. The preferred active ingredient for use herein is glycerine. Preferably, the weight ratio of humectant: carrier is from about 1:4 to about 3:1.

Also suitable as a highly cross-linked polymethacrylate copolymer is Microsponges 5647. This takes the form of generally spherical particles of cross-linked hydrophobic polymer having a pore size of from about 0.01 to about 0.05 μm and a surface area of 200–300 $m^2/g$. Again, it is preferably loaded with humectant in the levels described above.

The compositions of the invention can also contain a hydrophilic gelling agent at a level preferably from about 0.01% to about 10%, more preferably from about 0.02% to about 2%, and especially from about 0.02% to about 0.5%. The gelling agent preferably has a viscosity (1% aqueous solution, 20° C., Brookfield RVT) of at least about 4000 mPa.s, more preferably at least about 10,000 mPa.s and especially at least 50,000 mPa.s.

Suitable hydrophilic gelling agents can generally be described as water-soluble or colloidally water-soluble polymers, and include cellulose ethers (e.g. hydroxyethyl cellulose, methyl cellulose, hydroxypropylmethyl cellulose), polyvinylpyrrolidone, polyvinylalcohol, polyquaternium-10, guar gum, hydroxypropyl guar gum and xanthan gum.

Among suitable hydrophilic gelling agents are acrylic acid/ethyl acrylate copolymers and the carboxyvinyl polymers sold by the B.F. Goodrich Company under the trade mark of Carbopol resins. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are hydrophobically-modified cross-linked polymers of acrylic acid having amphipathic properties available under the Trade Name Carbopol 1382, Carbopol 1342 and Pemulen TR-1 (CTFA Designation: Acrylates/10–30 Alkyl Acrylate Crosspolymer). A combination of the polyalkenyl polyether cross-linked acrylic acid polymer and the hydrophobically modified cross-linked acrylic acid polymer is also suitable for use herein. Other suitable gelling agents suitable for use herein are oleogels such as trihydroxystearin and aluminium magnesium hydroxy stearate. The gelling agents herein are particularly valuable for providing excellent stability characteristics over both normal and elevated temperatures.

Neutralizing agents suitable for use in neutralizing acidic group containing hydrophilic gelling agents herein include sodium hydroxide, potassium hydroxide, ammonium hydroxide, monoethanolamine, diethanolamine and triethanolamine.

The make-up compositions herein can additionally comprise an emollient. Emollients suitable for the compositions of the present invention include natural and synthetic oils selected from mineral, vegetable, and animal oils, fats and waxes, fatty acid esters, fatty alcohols, alkylene glycol and polyalkylene glycol ethers and esters, fatty acids and mixtures thereof.

Suitable emollients for use herein include, for example, $C_1$–$C_{24}$ esters of $C_8$–$C_{30}$ saturated fatty acids such as isopropyl myristate, cetyl palmitate and octyldodecylmyristate (Wickenol 142), beeswax, saturated and unsaturated fatty alcohols such as behenyl alcohol and cetyl alcohol, hydrocarbons such as mineral oils, petrolatum and squalane, fatty sorbitan esters (see U.S. Pat. No. 3988255, Seiden, issued Oct. 26 1976), lanolin and lanolin derivatives, such as lanolin alcohol ethoxylated, hydroxylated and acetylated lanolins, cholesterol and derivatives thereof, animal and vegetable triglycerides such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil and $C_1$–$C_{24}$ esters of dimer and trimer acids such as diisopropyl dimerate, diisostearylmalate, diisostearyldimerate and triisostearyltrimerate. Also suitable for use as emollients include sugar esters prepared by the esterification of sugars at a mole ratio of esterification agent:sugar of at least 4:1, i.e. higher acyl sugar esters.

Preferred emollients are selected from cetearyl isononanoate, isopropyl palmitate, isopropyl isostearate, cetyl octanoate, cetyl acetate, trioctyl citrate, PEG isoceteth-3 acetate, dioctyl maleate, propylene glycol dicaprylate/dicaprate, caprylic/capric triglyceride, mineral oil, PPG-20 methylglucose ether, and lanolin alcohol, and mixtures thereof These emollients may be used independently or in mixtures and may be present in the composition of the present invention in an amount from about 1% to about 30% by weight, and preferably are present in an amount from about 5% to about 15% by weight of the total composition.

The compositions may also contain cholesterol. When present, cholesterol is incorporated at a level of from about 0.1% to about 5% by weight.

The composition may also contain additional materials such as, for example, fragrances, fillers such as nylon, sun-screens, preservatives, proteins, antioxidants, chelating agents and oil-in-water emulsifiers as appropriate.

Another optional component of the make-up composition is one or more ultraviolet absorbing agents. Ultraviolet absorbing agents, often described as sunscreening agents, can be present in a concentration in the range of between about 1% and about 12% by weight, based on the total weight of composition. Preferably, the UV absorbing agents constitute between about 2% and 8% by weight. More preferably, the UV absorbing agents can be present in the composition in a concentration range of between about 4% and about 6% by weight. Of the ultraviolet absorbing agents suitable for use herein, benzophenone-3, octyl dimethyl PABA (Padimate O) and mixtures thereof are particularly preferred.

A chelating agent can also be incorporated in the make-up composition. A chelating agent is preferably present in the composition in a concentration in the range of between about 0.02% to about 0.10% by weight, based on the total weight of the composition. Preferably, the chelating agent is present in a concentration in the range of between about 0.03% and about 0.07% by weight, based on the total weight of the composition. Among the chelating agents that may be included in the composition is trisodium EDTA.

Another optional but preferred component of the foundation composition is one or more preservatives. The preservative concentration in the foundation composition, based on the total weight of that composition, is in the range of between about 0.2% and about 0.8% by weight, preferably between about 0.4% and about 0.6% by weight. Suitable preservatives for use herein include diazolidinyl urea, methyl paraben and ethyl paraben, and mixtures thereof.

The make-up compositions of the present invention can be in the form of foundations, blushers, concealers, compact powders, and the like, preferably as foundations and blushers.

The following Table is provided to illustrate compositions of the make-up of the present invention:

EXAMPLES 1 to V

|  | I/% | II/% | III/% | IV/% | V% |
|---|---|---|---|---|---|
| A |  |  |  |  |  |
| Glycerin | 3.0 | 4.0 | 3.0 | 5.0 | 3.5 |
| Water |  |  | to 100 |  |  |
| B |  |  |  |  |  |
| Phenonip | 0.5 | 0.5 | 0.5 | 0.5 | 0.5 |
| Methyl paraben | 0.1 | 0.1 | 0.1 | 0.1 | 0.1 |
| $Na_4$ EDTA | 0.1 | 0.1 | 0.1 | 0.1 | 0.1 |
| C |  |  |  |  |  |
| Red Iron Oxide | 0.3 | 0.35 | 0.38 | 0.32 | 0.33 |
| Yellow Iron Oxide | 1.0 | 1.0 | 1.2 | 0.9 | 1.1 |
| Black Iron Oxide | 0.13 | 0.15 | 0.12 | 0.1 | 0.13 |
| Titanium Dioxide | 9.69 | 10.00 | 9.81 | 9.76 | 10.1 |
| Talc | 3.0 | 3.5 | 3.2 | 4.0 | 3.1 |
| D |  |  |  |  |  |
| Sucrose Monoleate (40% active) (OWA 1570 Ryoto Sugar) | 10.5 | 11.0 | 9.5 | 10.0 | 10.5 |
| E |  |  |  |  |  |
| Natrosol 250 HHR | 0.1 | 0.1 | 0.1 | 0.1 | 0.1 |
| Xanthan Gum | 0.15 | 0.2 | 0.18 | 0.15 | 0.15 |
| F |  |  |  |  |  |
| Sucrose Dilaurate | 0.0 | 0.0 | 0.0 | 0.75 | 0.0 |
| Ronoxan A | 0.06 | 0.05 | 0.06 | 0.06 | 0.05 |
| Cetyl Ricinoleate | 2.0 | 0.0 | 0.0 | 1.0 | 1.0 |
| Crodamol PMP | 8.0 | 0.0 | 0.0 | 4.0 | 4.0 |
| Cholesterol USP | 1.0 | 1.0 | 1.5 | 1.0 | 1.0 |
| DC 21330 | 15.0 | 25.0 | 20.0 | 20.0 | 20.0 |
| Polytrap 6603 | 2.0 | 0.0 | 0.0 | 2.0 | 2.0 |

In the first step, the components of phase A and the components of phase B are mixed together with high speed shear mixing until homogeneous. The components of phase C and then phase D are added to the mixture of phases A and B with mixing until dispersed. The components of phase E are added with mixing until homogeneous.

The resulting batch is heated to 70° C. while mixing is continued. The components of phase F are heated to about 70° C. and then are added to the aqueous mixture (A+B+C+D+E). The batch is mixed until homogeneous. The mixture is then cooled to room temperature with slow stirring.

The resulting make-up composition is ready for packaging.

The compositions of the examples exhibit improved product stability, improved oil/shine control and moisturisation effectiveness.

We claim:

1. A make-up composition in the form of an oil-in-water emulsion comprising:
   (a) from about 0.1% to about 30% by weight of volatile silicone oil and/or volatile hydrocarbon oil;
   (b) from about 0% to about 20% by weight of non-volatile oil;
   (c) from about 5% to about 25% by weight of pigment; and (d) from about 0.1% to about 20% by weight of organic amphiphilic material which is capable of forming smectic lyotropic liquid crystals in product or on the skin;

wherein the ratio of (a) to (d) is at least about 1.5:1.

2. A make-up composition according to claim 1 comprising at least about 20% by weight of volatile silicone oil and/or volatile hydrocarbon oil.

3. A make-up composition according to claim 1 wherein the non-volatile oil is selected from the group consisting of hydrocarbon waxes and oils, microcrystalline waxes, silicone waxes, fatty alcohols, esters of fatty acids with fatty alcohols and polyalkylene glycol ethers of fatty alcohols, and mixtures thereof.

4. A make-up composition according to any of claim 1 wherein the volatile silicone oil is selected from cyclic polyorganosiloxanes having viscosities of less than about 10 centistokes and linear polyorganosiloxanes having viscosities of less than about 5 centistokes at 25° C., and mixtures thereof.

5. A make-up composition according to claim 4 wherein the volatile silicone oil is selected from the group consisting of cyclic polydimethylsiloxanes containing from about 3 to about 9 silicon atoms and linear polydimethylsiloxanes containing from about 3 to about 9 silicon atoms.

6. A make-up composition according to claim 5 wherein the volatile silicone oil is a cyclic polydimethylsiloxane containing from about 3 to about 9 silicon atoms.

7. A make-up composition according to claim 1 wherein the volatile hydrocarbon oil is selected from the group consisting of isododecane, isohexadecane, isoeicosane, isodecane, decane, hexadecane, dodecane, tetradecane, octadecane, and mixtures thereof.

8. A make-up composition according to claim 1 wherein the amphiphilic material is selected from the group consisting of polyol esters, alkoxylated polyol esters and mixtures thereof.

9. A make-up composition according to claim 8 wherein the organic amphiphilic material is a sugar ester.

10. A make-up composition according to claim 9 wherein the organic amphiphilic material is sucrose monooleate.

11. A make-up composition according to claim 1 comprising from about 0.1% to about 15% by weight of the organic amphiphilic material.

12. A make-up composition according to claim 1 comprising from about 0.1% to about 10%, by weight of non-volatile oil.

13. A make-up composition according to claim 12 the non-volatile oil comprises a wax or a mixture of waxes and liquid oil having a melting completion temperature of at least about 30° C.

14. A make-up composition according to claim 12 wherein the non-volatile oil is selected from the group consisting of $C_8$–$C_{50}$ unsaturated fatty acids, esters of $C_8$–$C_{50}$ unsaturated fatty acids hydroxy-substituted $C_8$–$C_{50}$ unsaturated fatty acids, hydroxy-substituted esters of $C_8$–$C_{50}$ unsaturated fatty acids, PPG-2 myristyl ether propionate, and mixtures thereof.

15. A make-up composition according to claim 2 comprising at least about 25% by weight of volatile silicone oil.

16. A make-up composition according to claim 1 additionally comprising from about 0.1% to about 20%, by weight of humectant.

17. A make-up composition according to claim 16 wherein the humectant is glycerine.

18. A make-up composition according to claim 1 additionally comprising from about 0.1% to about 10% by weight of a matte finishing agent selected from the group consisting of silica, hydrated silica, mica, talc, polyethylene, titanium dioxide, bentonite, hectorite, kaolin, chalk, diatomaceous earth, attapulgite, and mixtures thereof.

19. A make-up composition according to claim 18 wherein the matte finishing agent is silica or hydrated silica.

20. A make-up composition according to claim 1 additionally comprising from about 0.1% to about 5% by weight of cholesterol.

21. A make-up composition according to claim 1 comprising from about 10% to about 60%, by weight of water.

22. A make-up composition according to claim 1 wherein the ratio of organic amphiphilic material to water is in the range from about 2:1 to about 1:6.

23. A make-up composition according to claim 1 wherein the ratio of organic amphiphilic material to total oil (a+b) is in the range from about 5:1 to about 1:5.

24. A make-up composition according to claim 1 additionally comprising from about 0.1% to about 10% by weight of a cross-linked hydrophobic acrylate or methacrylate copolymer.

25. A make-up composition according to claim 24 wherein the cross-linked hydrophobic copolymer is in the form of a lattice and wherein at least one active ingredient is dispersed uniformly throughout and entrapped within the copolymer lattice, the active ingredient being selected from the group consisting of skin compatible oils, skin compatible humectants, emollients, moisturizing agents and sunscreens.

26. A make-up composition according to claim 25 wherein the active ingredient is selected from the group consisting of humectants.

27. A make-up composition according to claim 5 wherein the volatile silicone oil is selected from cyclic polydimethylsiloxanes containing from about 4 to about 5 silicon atoms and linear polydimethylsiloxanes containing from about 3 to about 9 silicon atoms.

28. A make-up composition according to claim 12 comprising from about 2% to about 6% by weight of non-volatile oil.

29. A make-up composition according to claim 16 additionally comprising from about 1% to about 5% by weight of humectant.

30. A make-up composition according to claim 21 comprising from about 20% to about 50% by weight of water.

31. A make-up composition according to claim 22 wherein the ratio of organic amphiphilic material to water is in the range from about 1:1 to about 1:5.

32. A make-up composition according to claim 23 wherein the ratio of organic amphiphilic material to total oil (a+b) is in the range from about 1:1 to about 1:4.

33. A make-up composition according to claim 26 wherein the active ingredient is glycerine.

34. A make-up composition according to claim 8 wherein the organic amphiphilic material is a sugar ester selected from the group consisting of sucrose oleates, laurates and palmitates, and derivatives and mixtures thereof.

* * * * *